United States Patent [19]

Savostianoff et al.

[11] 3,996,226

[45] Dec. 7, 1976

[54] COMPOUNDS FOR GIVING FABRICS NON-STAIN PROPERTIES

[75] Inventors: Dimitri Savostianoff, Asnieres; Denise Dubos, Paris, both of France

[73] Assignee: Nobel Hoechst Chimie, Hauts-de-Seine, France

[22] Filed: Mar. 3, 1975

[21] Appl. No.: 555,036

Related U.S. Application Data

[62] Division of Ser. No. 328,061, Jan. 30, 1973, Pat. No. 3,927,024.

[30] Foreign Application Priority Data

Feb. 1, 1972 France ............................ 72.03355
Dec. 18, 1972 France ............................ 72.45091

[52] U.S. Cl. ................................ 260/249.6; 8/183
[51] Int. Cl.$^2$ ...................................... C07D 251/64
[58] Field of Search ................................ 260/249.6

[56] References Cited

UNITED STATES PATENTS 3,894,992 7/1975 Raynolds ........................ 260/249.6

*Primary Examiner*—John M. Ford
*Attorney, Agent, or Firm*—Karl W. Flocks

[57] ABSTRACT

The invention relates to new industrial chemical compounds imparting anti-soiling properties on cellulose and synthetic fabrics said compounds having the general formula:

$$A \begin{cases} (CH_2OR_1)_m \\ (CH_2OR_2)_n \\ (CH_2OR_3)_p \end{cases}$$

in which A is a radical resulting from the removal of at least three atoms of hydrogen replaceable by methylols on atoms of nitrogen of a compound capable of supplying aminoplasts; $R_1$ is either a hydrogen atom or an alkyl or acyl radical comprising less than 4 atoms of carbon; $R_2$ is an aliphatic alkyl or acyl radical comprising at least 10 atoms of carbon or aliphatic alkyl or acyl radical comprising at least 10 atoms of carbon or an alkyl radical comprising at least 2 atoms of carbon and at least one halogen substituent; $R_3$ is a radical resulting from the removal of a hydroxyl from the alcohol group of the addition product of 5 to 30 molecules of identical or different alkylene oxides on an alcohol or an acid; and *m*, *n* and *p* are equal to or greater than 1.

5 Claims, No Drawings

COMPOUNDS FOR GIVING FABRICS NON-STAIN PROPERTIES

This is a division of application Ser. No. 328,061, filed Jan. 30, 1975, now U.S. Pat. No. 3,927,024.

The present invention relates to new compounds for giving cellulose or synthetic fabrics non-stain properties.

The problem of protecting fabrics against staining and soiling has been the subject of numerous works which have led to the perfecting of products, the chemical nature of which is fairly varied and which, for this reason, have fairly different anti-stain properties. There may be cited for example the products which prevent fixing of certain types of stains on the fabrics during wear; this is the case of waterproof, oil-proof and anti-static products, the products which facilitate elimination of soil marks or stains by washing, especially "fatty" stains (so-called "soil release" products) and finally the products which prevent redepositing of dirt during washing. While certain products may be particularly active in one of these utilizations, they may not be without action in the others.

Amongst the products which facilitate elimination of stains and soiling by washing, the most important are the copolymers containing acrylic acid and the fluorocarbon resins. However, the greater part of the products at present marketed commercially has many disadvantages; they lack permanence, which means that the anti-staining effect diminishes rapidly during the course of successive washings; few are effective on synthetic fabrics and, generally speaking, almost all make the fabrics disagreeable to the touch.

The products according to the invention permit these disadvantages to be avoided to a great extent: they are permanent, effective on synthetic fabrics and give fabrics a soft feel.

The compounds forming the object of the present invention are substances which have the properties of a nonionic tensio-active agent and furthermore possess suitable reactive groups which enable them to become fixed on textiles. It has been found that such compounds give cellulose fabrics, synthetic fabrics and also mixed fabrics on which they are fixed advantageous non-staining properties.

More particularly, the compounds according to the invention are substances containing several atoms of methylolated nitrogen, partly or wholly etherified or esterified and further comprising in their molecule at least one water-repellent group and at least one hydrophilic group. According to the invention, these compounds thus contain, fixed on the methylol groups:

at least one water-repellent group represented by an aliphatic chain comprising a number of atoms of carbon greater than 10;

at least one hydrophilic chain, preferably obtained by polymerization of an alkylene oxide or of a mixture of alkylene oxides;

at least one reactive group enabling the compound to be fixed on textile fibres.

The compounds in question are represented by the following general formula:

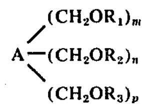

in which:

A represents a radical obtained by removing at least three atoms of hydrogen replaceable by methylols on nitrogens of a poly-nitrogenous compound;

$CH_2OR_1$ represents a reactive group acting on textile fibres;

$CH_2OR_2$ represents a water-repellent group;

$CH_2OR_3$ represents an hydrophilic group;

$R_1$ is either an atom of hydrogen or a lower acyl or alkyl radical comprising 1 to 4 atoms of carbon;

$R_2$ is an aliphatic acyl or alkyl radical with a long chain comprising at least 10 atoms of carbon or an alkyl radical comprising at least two atoms of carbon and at least one substituting halogen, such as a $(CH_2)_r$-$R_4$ in which $R_4$ is a perfluorinated alkyl radical and $r$ is a whole number equal to or greater than 1;

$R_3$ is a radical resulting from the removal of a hydroxyl from the alcohol group of the addition product of 5 to 30 molecules of identical or different alkylene oxides on an alcohol or an acid;

$m$, $n$ and $p$ may be equal to or greater than 1.

The compounds of the invention are prepared by the usual methods from the compounds $A\ (CH_2OR_1)_{m+n+p}$ by reacting the latter, successively with $R_2OH$ and then $R_3OH$ in the presence of an acid catalyst, the compounds $R_2OH$ and $R_3OH$ being utilized according to a number of mols corresponding respectively to $n$ and $p$.

The nitrogenous product which forms the radical A is preferably a product capable of supplying amino-plasts, such as for example, glycolurile, melamine, an alkyl or aryl diamino-4,6 s-triazine, dicyan-diamide, biuret and the like.

The radical $R_1$ is preferably a methyl or acetyl radical, the radical $R_2$ is an octadecyl radical, stearoyl or perfluoro-heptyl-methyl and the radical $R_3$ represents the chain of alkylene oxides obtained by the addition of ethylene oxide, propylene oxide or a mixture of the two on methanol or ethanol.

The compounds according to the invention are applied to the fabrics by impregnation in a full bath followed by a fulling in the presence of an acid catalyst or one capable of liberating an acid. They may also be applied at the same time as textile resins of the same type as those used to improve the non-creasing properties of cellulose fabrics or to improve the feel of synthetic fabrics, or any other auxiliary textile resin.

It is, of course, recommended to avoid using them with products known for their aptitude in attracting stains, such as certain silicones or acrylic resins.

After drying in the vicinity of 100° C and condensation at about 150° C, there are obtained dressings which withstand successive washings and which facilitate the elimination of stains by washing, even in the presence of textile resins. In addition, the fabrics thus treated are soft and agreeable to the touch.

The following non-limitative examples will give a more precise idea of the compounds according to the invention and their application as non-stain anti-soiling agents.

EXAMPLE 1

318 grams (1 mol) of tetra-methoxy-methyl-glycolurile are heated while stirring with 271 grams (1 mol) of octadecanol-1 in the presence of 0.200 grams of paratoluene-sulphonic acid up to 80°–100° C. The methanol formed during the course of the reaction is collected. When 32 grams (1 mol) of methanol have been collected, there are added 452 grams (about 1 mol) of an alcohol obtained by adding 10 molecules of ethylene oxide to 1 molecule of methanol and 4.5 grams of para-toluene-sulphonic acid. The mixture is heated to 90°–100° C until 32 grams (1 mol) of methanol have been distilled. After cooling, there are obtained 950 grams of a waxy mass composed essentially of dimethoxy-methyl, octadecyl-oxy-methyl, methoxy-deca (ethylenoxy)-methyl-glycolurile.

EXAMPLE 2

The procedure is the same as that described in Example 1, but instead of methoxy-nona (ethylenoxy)-ethanol, there are emoployed 748 grams (about 1 mol) of methoxypentadeca (ethylenoxy) ethanol obtained by the addition of 16 molecules of ethylene oxide to 1 molecule of methanol. There are thus obtained 1250 grams of a waxy mass composed essentially of dimethoxy-methyl, octa-decyloxy-methyl, methoxy-hexadeca(ethylenoxy)-methyl-glycolurile.

EXAMPLE 3

The operation is the same as in Example 1, but the tetramethoxy-methyl-glycolurile is replaced by 390 grams (1 mol) of hexamethoxy-methyl-melamine. There are thus obtained 1040 grams of tetramethoxy-methyl-octadecyloxy-methyl-methoxy-deca(ethylenoxy)-methyl-melamine.

EXAMPLE 4

The procedure is the same as in Example 2, using instead of the tetramethoxy-methyl-glycolurile, 390 grams (1 mol) of hexamethoxy-methyl-melamine. In this way there are obtained 1340 grams of tetramethoxy-methyl-octadecyloxy-methyl-methoxy-hexadeca(ethylenoxy)-methyl-melamine.

EXAMPLE 5

To 318 grams (1 mol) of tetramethoxy-methyl-glycolurile, there are added 284 grams (1 mol) of stearic acid and the mixture is heated under vacuum at 150°–180° C until the acid number of the reaction mixture is lower than 5. The mixture is then cooled to 70° C and there are added 452 grams (about 1 mol) of methoxy-nona(ethylenoxy)ethanol together with 4 grams of para-toluene-sulphonic acid. The mixture is heated at 80°–100° C until the elimination of 32 grams (1 mol) of methanol. There are obtained 950 grams of dimethoxy-methyl-stearoyloxy-methyl-methoxy-deca(ethylenoxy) methyl-glycolurile.

EXAMPLE 6

The first part of the operation is carried out as described in Example 5 but in the second part, the methoxynona-(ethylenoxy)-ethanol is replaced by 748 grams (about 1 mol) of methoxy-penta-deca(ethylenoxy)-ethanol, which gives 1250 grams of a product constituted essentially by dimethoxy-methyl-stearoyloxy-methyl-hexadeca(ethylenoxy)-methyl-glycolurile.

EXAMPLE 7

The procedure is the same as for Example 5 for the first part of the reaction, but the tetramethoxy-methyl-glycolurile is replaced by hexamethoxy-methyl-melamine, that is to say stearic acid is reacted on the latter product, and then for the second part as in Example 1, that is to say that condensation is carried out with the methoxy-nona(ethylenoxy)-ethanol.

There are thus obtained 1055 grams of tetramethoxy-methyl-stearoyloxy-methyl-methoxy-deca(ethylenoxy)-methyl melamine.

EXAMPLE 8

The operation is the same as for Example 5 for the first part of the reaction but by replacing tetramethoxy-methyl-glycolurile by hexamethoxy-methyl-melamine on which stearic acid is reacted. In the second part of the reaction, the methoxy-penta-deca-(ethylenoxy)-ethanol is reacted and there are thus obtained 1350 grams of tetramethoxy-methyl-stearoyloxy-methyl-methoxy-hexadeca (ethylenoxy)-methyl-melamine.

EXAMPLE 9

A polyester-cotton fabric 67/33 is treated by the product of Example 1 under the following conditions:

The impregnation is effected in a full bath in a solution with a pH value of 4.5–5 containing per liter:

| | |
|---|---|
| The product of Example 1 | 50 grams |
| The NKC catalyst of Nobel Hoechst/Chimie (with a base of magnesium chloride) | 5 grams |

The impregnation is followed by a fulling operation with a liquid extraction rate of 75%. After drying at 120° C, the product is condensed for 3½ minutes at 155° C. and then the non-soiling effect is evaluated.

METHOD EMPLOYED FOR THE EVALUATION OF THE NON-SOILING EFFECT

The method employed in close to that forming the subject of the AATCC Standard No. 130, 1969. The test is however, more severe, other stains having been added to those provided by this Standard. It consists of carrying out on the fabric to be examined stains having the following compositions:

| | | |
|---|---|---|
| 1. | Mixture | |
| | Active carbon (black Acticarbone 3 S of SOBREP) | 2 grams |
| | "NUJOL" vaseline oil | 20 grams |
| | Lanoline | 1 gram |
| | Trichlor-ethylene | 10 grams |
| 2. | Arachis oil. | |
| 3. | Drained automobile engine oil. | |

The fabric thus soiled is kept for 4 hours before washing. The washing is carried out for 12 minutes at 60° C, using as a detergent 3 grams per liter of a commercial product "SUPER BOZIL" of NOBEL BOZEL.

After drying for 45 minutes in a drier of the "tumble-dry" type, the washed samples are compared with the "Standard replicas" numbered from 1 to 5 by order of decreasing visibility of the stain:

No. 1, the stain is very visible;

No. 5, the stain has practically disappeared.

In order to define further the results obtained, the FIGS. 1 to 5 have been given signs of + and −, giving an estimate more or less than the figure indicated.

METHOD USED FOR THE EVALUATION OF THE PERMANENCE OF THE ANTI SOILING EFFECT

The permanence of the anti-soiling treatment is assessed by carrying out on other samples of fabric treated with the anti-soiling dressing, on the one hand a series of 3 washings and, on the other, a series of 10 washings at 60° C, following the AATCC Standard 88E of 1969, and then drying for 45 minutes at 70° C in the Tumble-Dry. The samples are then conditioned for 24 hours at 20° C ± 2 in an atmosphere at 65% ± 1 of humidity, after which they are subjected to an estimation of the antisoiling effect following the method described above.

The results obtained in the assessment of the anti-soiling effect and of its permanence after 3 washings and after 10 washings, expressed by FIGS. of 1 to 5, are collected together in the following TAble in comparison with an untreated fabric:

| Stains | Untreated fabric | Non-soiling treated fabric | | |
|---|---|---|---|---|
| | | Initial test | Test after 3 washings | Test after 10 washings |
| Mixture 1 | 2 | 4 | 4 | $4^-$ |
| Arachis oil | 2 | 4 | 4 | $3^+$ |
| Motor oil | 1 | 2 | $2^-$ | $1^+$ |

The fabric treated retains practically no trace of the stains of mixture 1 and of the arachis oil, and this non-soiling effect is wholly preserved after 3 washings; it is still very considerable after 10 washings.

EXAMPLE 10

A polyester/cotton fabric 67/33 is treated at the same time with the product of Example 1 and a textile resin with a base of dymethylol-dihydroxy-ethylene-urea. The conditions of application are the same as those of Example 9, the bath having the following composition in grams per liter:

| | |
|---|---|
| Product of Example 1 | 50 grams |
| ARKOFIX NGF of Nobel Hoechst Chimie | 150 grams |
| Catalyst NKC of Nobel Hoechst Chimie | 50 grams |

A comparative test is also carried out with the same bath in the absence of the product of Example 1 that is to say solely with the textile resin and the catalyst. There are obtained the results as set out in the Table below:

| Stains | Untreated fabric | Fabric treated with ARKOFIX NBF | | | Fabric treated with ARKOFIX + Product of Example 1 | | |
|---|---|---|---|---|---|---|---|
| | | Initial test | Test after 3 washings | Test after 10 washings | Initial test | Test after 3 washings | Test after 10 washings |
| Mixture 1 | 2 | $2^-$ | $2^+$ | $2^+$ | $4^+$ | 3 | $3^+$ |
| Arachis oil | 2 | 2 | $2^+$ | $2^-$ | $4^+$ | $3^+$ | 3 |
| Motor oil | 1 | $1^-$ | 1 | $1^-$ | 3 | $2^+$ | $2^-$ |

The non-soiling effect is also very definite.

EXAMPLE 11

A fabric of 100% polyamide is treated with the product of Example 1 under the same conditions as in Example 9, but with a liquid extraction rate of 55% and with a bath having the following composition in grams per liter:

| | |
|---|---|
| The product of Example 1 | 65 grams |
| Catalyst NKC of Nobel Hoechst Chimie | 6.5 grams |

The results obtained are as follows:

| Stains | Untreated fabric | Non-soiling treated fabric | | |
|---|---|---|---|---|
| | | Initial Test | Test after 3 washings | Test after 10 washings |
| Mixture 1 | 3 | $5^-$ | 4 | $4^-$ |
| Arachis oil | $2^+$ | $4^+$ | $4^-$ | $4^-$ |
| Motor Oil | 2 | $3^+$ | 3 | $3^-$ |

On pure synthetic textiles, the product is therefore also shown to be very effective.

EXAMPLE 12

A fabric of 100% polyamide is treated with the product of Example 1 under the same conditions as in Example 9, but with a liquid extraction rate of 55% and with a bath containing, in addition to the product of Example 1, a textile resin with a base of methylolated melamine having a composition in grams per liter:

| | |
|---|---|
| The product of Example 1 | 65 grams |
| ARKOFIX NM of Nobel HOECHST Chimie | 40 grams |
| NKC catalyst of Nobel Hoechst Chimie | 18.5 grams |

A comparative test is carried out with a bath of the same composition but without the product of Example 1.

The following results were obtained:

| Stains | Untreated fabric | Fabric treated with ARKOFIX NM | | | Fabric treated with ARKOFIX NM + product of Example 1 | | |
|---|---|---|---|---|---|---|---|
| | | Initial test | Test after 3 washings | Test after 10 washings | Initial test | Test after 3 washings | Test after 10 washings |
| Mixture 1 | 3 | 3 | 3+ | 2 | 4+ | 4− | 4− |
| Arachis oil | 2+ | 2− | 2 | 2− | 4 | 3+ | 3 |
| Motor oil | 2 | 2− | 2 | 1 | 3+ | 3− | 3− |

The non-soiling product is therefore also effective on synthetic textiles in the presence of a textile resin.

EXAMPLE 13

A polyester/cotton fabric 67/33 is treated by the product of Example 4 under the same conditions as in Example 9, but with a bath having the following composition, expressed in grams per liter:

| | |
|---|---|
| Product of Example 4 | 50 grams |
| Catalyst NKN of Nobel Hoechst Chimie (comprising zinc nitrate) | 5 grams |

The results obtained are as follows:

| Stains | Treated non-soiling fabric | | | |
|---|---|---|---|---|
| | Untreated fabric | Initial test | Test after 3 washings | Test after 10 washings |
| Mixture 1 | 2 | 4 | 3+ | 3+ |
| Arachis oil | 2 | 4− | 3− | 3+ |
| Motor oil | 1 | 3+ | 3− | 2+ |

EXAMPLE 14

A polyester/cotton fabric 67/33 is treated at the same time with the product of Example 4 and with a textile resin comprising dimethylol-dihydroxy-ethyleneurea, utilizing the conditions of application of Example 9, but with a bath having the following composition in grams per liter:

| | |
|---|---|
| Product of Example 4 | 50 grams |
| ARKOFIX NGF of Nobel Hoechst Chimie | 150 grams |
| Catalyst NKC of Nobel Hoechst Chimie | 50 grams |

A comparative test is carried out with the same bath but without the product of Example 4. These tests gave the following results:

| Stains | Untreated fabric | Fabric treated with ARKOFIX NGF | | | Fabric treated with ARKOFIX NGF + product of Example 4 | | |
|---|---|---|---|---|---|---|---|
| | | Initial test | Test after 3 washings | Test after 10 washings | Initial test | Test after 3 washings | Test after 10 washings |
| Mixture 1 | 2 | 2− | 2+ | 2+ | 4+ | 3+ | 3+ |
| Arachis oil | 2 | 2 | 2+ | 2− | 4+ | 3 | 3 |
| Motor oil | 1 | 1− | 1 | 1− | 3+ | 3− | 2− |

EXAMPLE 15

A fabric of 100% polyamide is treated under the conditions of Example 9 but with a liquid extraction rate of 55% with a bath containing, in grams per liter:

| | |
|---|---|
| Product of Example 4 | 65 grams |
| Zinc chloride | 3 grams |

The following results were obtained:

| Stains | Fabric treated | | | |
|---|---|---|---|---|
| | Untreated fabric | Initial Test | Test after 3 washings | Test after 10 washings |
| Mixture 1 | 3 | 5− | 4+ | 4+ |
| Arachis oil | 2+ | 4+ | 4+ | 4 |
| Motor oil | 2 | 3+ | 3 | 3− |

EXAMPLE 16

A fabric of 100% polyamide is treated according to the conditions of Example 9 but with a liquid extraction rate of 55% and utilizing a bath containing, in addition to the product of Example 4, a resin comrising methylolated melamine in the following proportions in grams per liter:

| | |
|---|---|
| Product of Example 4 | 65 Grams |
| ARKOFIX NM of Nobel Hoechst Chimie | 40 Grams |
| Zinc chloride | 7 Grams |

A comparative test is also carried out with a bath of the same composition but without the product of Example 4. The Table below summarizes the values obtained:

| | | Fabric Treated with ARKOFIX NM | | | Fabric Treated with ARKOFIX NM + product of Example 4 | | |
|---|---|---|---|---|---|---|---|
| Stains | Untreated fabric | Initial Test | Test after 3 washings | Test after 10 washings | Initial test | Test after 3 washings | Test after 10 washings |
| Mixture 1 | 3 | $2^+$ | $2^+$ | 2 | $5^-$ | $3^+$ | $3^+$ |
| Arachis oil | $2^+$ | $2^+$ | $3^-$ | $1^+$ | $4^+$ | $4^-$ | $3^+$ |
| Motor oil | 2 | 2 | 2 | 1 | $3^+$ | 3 | $2^+$ |

It is definitely clear from Examples 9 to 16 that the products of the invention have an anti-soiling effect on cellulose fabrics and on synthetic fabrics and that this effect withstands washing. In addition, all the samples of these examples treated with the product according to the invention have a soft feel.

EXAMPLE 17

318 grams (1 mol) of tetramethoxy-methyl-glycolurile are heated to 85–95° C. while stirring with 496 grams (1 mol) of an alcohol obtained by adding 10 molecules of a mixture of ethylene-oxide-propylene oxide in the proportions of 1 to 1 to one molecule of methanol, the whole in the presence of 4 grams of paratoluene sulphonic acid.

The methanol formed during the course of the reaction is collected by distillation under vacuum. When 32 grams or 1 mol of methanol have been collected, there are added 271 grams (1 mol) of octadecanol together with 0.2 gram of paratoluene sulphonic acid. The mixture is heated to 90°–100° C until 32 grams (1 mol) of methanol have been distilled. After cooling, there are obtained 1000 grams of a product which is diluted in water at 33% after it has been neutralized with triethanolamine.

EXAMPLE 18

The procedure is the same as for Example 17, but there are employed in the first part 738 grams (1 mol) of alcohol obtained by adding 15 molecules of a mixture of ethylene and propylene oxides in the proportions of 1 to 1, on 1 molecule of methanol.

There are thus obtained 1250 grams of product which are diluted in water to 33% after having neutralized it with triethanolamine.

EXAMPLE 19

The procedure is carried out as in Example 17, but the alcohol of the first portion of the reaction is replaced by 1160 grams (1 mol) of an alcohol obtained by addition of 20 mols of a mixture of ethylene oxide and propylene oxide on 1 molecule of butanol. There are thus obtained 1600 grams of product which are treated in the same manner as in the previous Example.

EXAMPLE 20

The same procedure is followed as in Example 17, but instead of tetramethoxy-methyl-glycolurile, there is utilized 390 grams (1 mol) of hexamethoxy-methylmelamine. After reaction there are obtained 1060 grams of a product which is neutralized with triethanolamine and which is diluted to 33% in water.

EXAMPLE 21

The operation is the same as in Example 18, but utilizing 390 grams (1 mol) of hexamethoxy-methylmelamine instead of tetramethoxy-methyl-glycolurile. There are obtained 1300 grams of a product which is diluted to 33% in water after it has been neutralized with triethanolamine.

EXAMPLE 22

The operation is the same as for Example 19, with replacing the tetramethoxy-methyl-glycolurile by 390 grams (1 mol) of hexamethoxy-methyl-melamine. There are obtained 1600 grams of a product which is diluted to 33% in water after having been neutralized by triethanolamine.

EXAMPLE 23

A polyester/cotton fabric 67/33 is treated with the product of Example 20 under the same conditions as in Example 9, the concentration of the bath in the product of Example 20 being 50 grams per liter expressed in 10% product. The methods used for the assessment of the non-soiling effect and of the permanence of this effect being the same as in Example 9, another sample of the same fabric was treated under the same conditions with the product of Example 21. The results obtained were as follows:

| | | Non-soiling treated fabric | | | | |
|---|---|---|---|---|---|---|
| | | Product of Example 20 | | Product of Example 21 | | |
| Stains | Untreated fabric | Initial Test | Test after 3 washings | Initial Test | Test after 3 washings | Test after 10 washings |
| Mixture 1 | 2 | $4^-$ | $3^+$ | $4^+$ | $2^+$ | $2^+$ |
| Arachis oil | 2 | 5 | 3 | $4^+$ | $3^-$ | $2^-$ |
| Motor oil | 1 | $3^+$ | $2^+$ | 3 | $2^+$ | $1^+$ |

EXAMPLE 24

The previous test is repeated with the same products of Examples 20 and 21, but under the conditions of Example 10, mainly in the presence of a textile resin ARKOFIX NGF. The results obtained were as follows:

| Stains | Fabric treated with ARKOFIX NGF Initial test | Test after 3 washings | Test after 10 washings | Fabric treated with ARKOFIX + product of Example 20 Initial test | Test after 3 washings | Fabric treated with ARKOFIX + product of Example 21 Initial test | Test after 3 washings | Test after 10 washings |
|---|---|---|---|---|---|---|---|---|
| Mixture 1 | 2⁻ | 2⁺ | 2⁺ | 4 | 2⁺ | 4 | 3⁻ | 2⁺ |
| Arachis oil | 2 | 2⁺ | 2⁻ | 4⁻ | 2⁺ | 4 | 3⁻ | 3⁻ |
| Motor oil | 1 | 1 | 1⁻ | 2 | 2⁻ | 2⁺ | 2⁺ | 2 |

| Stains | Fabric treated with ARKOFIX NM Initial test | Test after 3 washings | Test after 10 washings | Fabric treated with ARKOFIX + product of Example 20 Initial test | Test after 3 washings | Fabric treated with ARKOFIX + product of Example 21 Initial test | Test after 3 washings | Test after 10 washings |
|---|---|---|---|---|---|---|---|---|
| Mixture 1 | 2⁺ | 2⁻ | 2⁻ | 4⁻ | 3 | 4⁺ | 3 | 3⁻ |
| Arachis oil | 2 | 2 | 2⁻ | 3⁺ | 3 | 4⁻ | 3⁻ | 3⁻ |
| Motor oil | 2 | 2⁺ | 2 | 3 | 3 | 3⁺ | 2⁺ | 2⁺ |

EXAMPLE 25

A 100% polyamide fabric is treated under the same conditions as in Example 11 with a bath having the following composition in grams per liter:

| | |
|---|---|
| Product of Example 20 (expressed in 100%) | 50 grams |
| Zinc chloride | 3 grams |

An identical fabric is treated under the same conditions with the product of Example 21, and the results obtained are as follows:

| Stains | Untreated fabric | Fabric treated with Product of Example 20 Initial test | Test after 3 washings | Fabric treated with Product of Example 21 Initial test | Test after 3 washings | Test after 10 washings |
|---|---|---|---|---|---|---|
| Mixture 1 | 3 | 5 | 3⁺ | 5 | 3⁺ | 3 |
| Arachis oil | 2⁺ | 4 | 3 | 5 | 3⁻ | 3⁻ |
| Motor oil | 2 | 3⁺ | 2⁺ | 4 | 3 | 2⁺ |

EXAMPLE 26

The 100% polyamide fabric is treated under the conditions of Example 12 with a bath having the following composition in grams per liter:

—Product of Example 20 (in 100%) .......... 50 grams
—ARKOFIX NM .......... 30 grams
—Zinc chloride .......... 6 grams An identical fabric is treated under the same conditions with the product of Example 21.

The results obtained are as follows:

EXAMPLE 27

318 grams (1 mol) of tetramethoxy-methyl-glycolurile are heated while stirring with 452 grams (1 mol) of an alcohol derived from the addition of 9.55 molecules of ethylene oxide on 1 molecule of methanol and 1.5 grams of paratoluene sulphonic acid. The mixture is heated under vacuum (20 mm. Hg) at 90°–100° C until there are obtained 32 grams (1 mol) of methanol. There are then added 400 grams (1 mol) of perfluoro-heptyl-methanol. Heating is carried out at 120° C under a slight vacuum (0.2 kg/sq cm). After cooling there is obtained 1 kg of a product composed essentially of: dimethoxy-methyl-perfluoro-heptyl-methylenoxy-methyl-methoxy-deca(ethylene-oxy)-methyl-glycolurile.

EXAMPLE 28

The operation is carried out as in Example 27, but the tetramethoxy-methyl-glycolurile is replaced by 390 grams (1 mol) of hexamethoxy-methyl-amine. There are thus obtained 1.17 kg of tetramethoxy-methyl-perfluoro-heptyl-methylene-oxy-methyl-methoxy-deca(ethylene-oxv)-methyl-melamine.

EXAMPLE 29

A polyester/cotton fabric 67/33 is treated with the product of Example 27 in the presence of a so-called "reactive" textile resin under the following conditions: the impregnation is carried out in a full bath of a solution containing, per liter:

| | Test 1 | Test 2 |
|---|---|---|
| Product of Example 27 | 10 grams | 25 grams |
| ARKOFIX NG of Nobel Hoechst Chimie (comprising dimethylol-dihydroxy-ethylene-urea) | 80 grams | 80 grams |
| Catalyst NKN of Nobel Hoechst Chimie | | |

-continued

| | Test 1 | Test 2 |
|---|---|---|
| (comprising zinc nitrate) | 16 grams | 16 grams |

The impregnation is followed by a fulling process with a liquid extraction rate of 75%. After drying at 120° C, the product is condensed for 3 minutes at 160° C and then conditioned for 24 hours at 20° C in an atmosphere containing 65% humidity.

The following tests were carried out on the fabric thus treated:

1. Estimate of the anti-soiling effect (AATCC test)

2. Estimate of the anti-soiling effect and of the non-re-deposit effect of the soiling substance (CASSELLA test).

1. Method used to estimate the anti-soiling effect (AATCC test)

This method is that described in Example 9.

2. Method used to estimate the anti-soiling effect and the non-re-deposit effect of the soiling substance (CASSELLA test).

The method utilized is that described by Dr. R. KLEBER "Soil release, Problematik und Aspekte" Textil Praxis 1969 — Heft 1, p.49. It consists of applying mayonnaise with 80% of fat content to the middle of the fabric to be tested, and then, after drying for 2 hours, of dipping the sample into an aqueous dispersion at 1% of smoke black; after drying for 2 hours in air, the sample is washed by hand for 10 minutes at 60° C with a detergent, rinsed and then dried. The anti-soiling effect is assessed by the elimination by washing of the stain of mayonnaise and the anti-re-deposit effect of the soiling substance by the coloration of the fabric outside the stain of mayonnaise.

For the sake of convenience, the results have been expressed by numbers of 1 to 6, comparing with standards prepared by the Applicants for that purpose.

| ANTI-SOILING EFFECT (Stain of mayonnaise). | |
|---|---|
| No. 1 | - The stain is completely black (no anti-soiling effect). |
| No. 2 | - The stain is represented by a large black ring. |
| No. 3 | - The stain consists of a black ring smaller than for No. 2. |
| No. 4 | - The stain consists of a grey ring smaller than No. 3. |
| No. 5 | - The stain is represented by a grey ring which can hardly be seen. |
| No. 6 | - There is no trace of the stain of mayonnaise. |

| | |
|---|---|
| No. 1 | The fabric is black (no anti-redeposit effect of the soiling substances). |
| No. 6 | The fabric is clean. |

The FIGS. 2 to 5 correspond to different gray aspects of the fabric, the No. 2 being the deepest grey.

In addition to the above methods 1 and 2, the permanence to washing of the anti-soiling and anti-redeposit effect is estimated. For this purpose, samples of fabrics treated with the anti-soiling dressing have been subjected either to a series of 5 washings or to a series of 15 washings before undergoing the tests 1 or 2. Each of these washings was carried out in a washing machine for 10 to 12 minutes at 60° C, followed by drying for 45 minutes at 70° C in a "Tumble-Dry" machine.

The results obtained in the various tests in the treated fabric are collected in the Tables given below in comparison with a fabric which is untreated or treated only with "reactive" resin.

1-ANTI-SOILING EFFECT (AATCC TEST)

| Stains | Fabric treated with ARKOFIX NG only | Anti-soiling treated fabric: Initial test | | Test after 5 washings | | Test after 15 washings | |
|---|---|---|---|---|---|---|---|
| | | 10g/l | 25g/l | 10g/l | 25g/l | 10g/l | 25g/l |
| Mixture 1 | $2^-$ | $4^-$ | 4 | $3^+$ | $3^+$ | $3^+$ | $3^+$ |
| Arachis oil | $1^+$ | $5^-$ | $5^-$ | 4 | $4^+$ | $4^-$ | $4^-$ |
| Motor oil | 1 | $3^-$ | 3 | $3^-$ | $3^-$ | $3^-$ | 3 |

2 - ANTI-SOILING EFFECT AND ANTI-REDEPOSIT EFFECT OF SOILING SUBSTANCE (CASSELLA Test)

| Stains | Untreated fabric | Anti-soiling treated fabric: Initial test | | Test after 5 washings | | Test after 15 washings | |
|---|---|---|---|---|---|---|---|
| | | 10g/l | 25g/l | 10g/l | 25g/l | 10g/l | 25g/l |
| Anti-soiling | $2^+$ | $5^-$ | $5^+$ | 5 | 5 | $4^-$ | $3^+$ |
| Anti-redeposit of soiling substances | $2^+$ | $5^+$ | 5 | $3^+$ | $4^+$ | $3^+$ | $4^+$ |

The product of Example 1 thus had advantageous anti-soiling and anti-redeposit properties; in addition, the feel of the samples is soft and agreeable.

EXAMPLE 30

A polyester/cotton fabric 67/33 is treated under the same conditions as in Example 29 but replacing the product of Example 27 by the product of Example 28;

the results obtained are collected in the following Tables:

1. ANTI-SOILING EFFECT (AATCC TEST)

| Stains | Untreated fabric | Anti-soiling treated fabric: Initial test | | Test after 5 washings | | Test after 15 washings | |
|---|---|---|---|---|---|---|---|
| | | 10g/l | 25g/l | 10g/l | 25g/l | 10g/l | 25g/l |
| Mixture 1 | $2^-$ | $4^-$ | 4 | $3^+$ | $4^-$ | $3^+$ | $3^+$ |
| Arachis oil | $1^+$ | $4^+$ | $5^-$ | $4^-$ | 4 | 3 | 3 |
| Motor oil | 1 | 2 | $3^-$ | $2^+$ | 2 | $1^+$ | $2^-$ |

2 - ANTT-SOILING EFFECT AND ANTI-REDEPOSIT EFFECT OF SOILING SUBSTANCES (CASSELLA Test)

| Effect | Untreated fabric | Anti-soiling treated fabric: Initial test | | Test after 5 washings | | Test after 15 washings | |
|---|---|---|---|---|---|---|---|
| | | 10g/l | 25g/l | 10g/l | 25g/l | 10g/l | 25g/l |
| Anti-soiling | $2^+$ | $4^-$ | 4 | $4^-$ | $4^-$ | $3^+$ | $4^-$ |
| Anti-redeposit of soiling substances | $2^+$ | $4^+$ | $4^-$ | 3 | $3^-$ | $2^+$ | $3^-$ |

The product of Example 28 also has valuable anti-soiling and anti-redeposit properties.

It will of course be understood that the present invention has been described solely by wav of explanation and not in any limitative sense and that any useful modification may be made thereto without thereby departing from its scope as defined in the appended Claims.

We claim:

1. A compound of the formula:

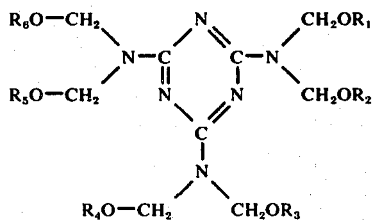

wherein at least one of $R_1$, $R_2$, $R_3$, $R_4$, $R_5$ and $R_6$ is selected from the group consisting of alkyl and alkanoyl radicals having at least 10 carbons and alkyl radicals having at least 2 carbons and at least one halogen substituent; at least one of $R_1$, $R_2$, $R_3$, $R_4$, $R_5$ and $R_6$ is the radical resulting from the removal of a hydroxyl from the alcohol group of the addition product of 5 to 30 molecules of identical or different alkylene oxides on an alcohol or an acid; and the other remaining $R_1$, $R_2$, $R_3$, $R_4$, $R_5$ and $R_6$ are hydrogen or a lower alkanoyl or alkyl radical having less than 4 carbons.

2. A compound in accordance with claim 1 wherein one of $R_1$, $R_2$, $R_3$, $R_4$, $R_5$ and $R_6$ is $(-CH_2)_r-R_7$ in which $R_7$ is a perfluorinated alkyl of 6-12 carbons and r is a whole number equal to 1-4.

3. A compound in accordance with claim 1 wherein $R_1$, $R_2$, $R_3$, and $R_4$, are each methyl; $R_5$ is octadecyl or stearoyl; and $R_6$ is a radical resulting from the removal of OH from the alcohol group of the addition product selected from the group of addition products of 10 and 16 molecules of ethylene oxide on methanol.

4. A compound in accordance with claim 2 wherein $R_1$, $R_2$, $R_3$, and $R_4$ are each methyl; $R_5$ is perfluoro-heptyl-methyl and $R_6$ is a radical resulting from the removal of OH from the alcohol group of the addition product of 8 to 10 molecules of ethylene oxide on methanol.

5. A compound in accordance with claim 1 wherein at least one of $R_1$, $R_2$, $R_3$, $R_4$, $R_5$ and $R_6$ is $(AO)_mR_7$ wherein A is ethylene or propylene, m is an integer of 5 to 30 and $R_7$ is an alkyl of 1-4 carbons.

* * * * *